United States Patent
Wall

(10) Patent No.: US 11,219,534 B2
(45) Date of Patent: Jan. 11, 2022

(54) SPINAL IMPLANT SYSTEM AND METHOD

(71) Applicant: Warsaw Orthopedic, Inc., Warsaw, IN (US)

(72) Inventor: Daniel Paxton Wall, Cordova, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 40 days.

(21) Appl. No.: 16/513,399

(22) Filed: Jul. 16, 2019

(65) Prior Publication Data
US 2021/0015630 A1 Jan. 21, 2021

(51) Int. Cl.
*A61F 2/46* (2006.01)
*A61F 2/44* (2006.01)
*A61B 34/20* (2016.01)
*A61F 2/30* (2006.01)
*A61B 90/00* (2016.01)

(52) U.S. Cl.
CPC ............ *A61F 2/4611* (2013.01); *A61B 34/20* (2016.02); *A61F 2/446* (2013.01); *A61B 90/37* (2016.02); *A61B 2034/2072* (2016.02); *A61F 2002/3085* (2013.01); *A61F 2002/30143* (2013.01); *A61F 2002/30995* (2013.01); *A61F 2002/4627* (2013.01); *A61F 2002/4629* (2013.01); *A61F 2002/4632* (2013.01)

(58) Field of Classification Search
CPC .... A61F 2/446; A61F 2/4611; A61B 17/8875; A61B 17/8886; A61B 17/8888; A61B 17/8894; A61B 17/7082
See application file for complete search history.

(56) References Cited

U.S. PATENT DOCUMENTS

| | | | |
|---|---|---|---|
| 6,725,080 B2 * | 4/2004 | Melkent | A61B 5/06 600/424 |
| 8,394,108 B2 * | 3/2013 | McLean | A61B 17/7082 606/104 |
| 8,784,431 B1 * | 7/2014 | Harder | A61B 17/7082 606/104 |
| 2002/0138079 A1 * | 9/2002 | Cohen | A61B 17/025 606/99 |
| 2010/0198272 A1 * | 8/2010 | Keyer | A61B 17/7082 606/302 |

(Continued)

OTHER PUBLICATIONS

WIPO ISA/KR Intl. Searching Authority Korean Patent Office, PCT/US2020/041908, Intl. Search Report and Written Opinion, dated Oct. 28, 2020.

*Primary Examiner* — Eduardo C Robert
*Assistant Examiner* — Steven J Cotroneo
(74) *Attorney, Agent, or Firm* — Sorell, Lenna & Schmidt, LLP

(57) ABSTRACT

A surgical instrument comprises an outer sleeve including an inner surface that defines a cavity. An inner shaft is fixed with the outer sleeve and extends within the cavity. The inner shaft includes a drive engageable in a torque interface with a first mating surface of a bone fastener. An inner sleeve is disposed between the inner shaft and the outer sleeve. The inner sleeve is axially fixed and rotatable relative to the outer sleeve. The inner sleeve includes an element connectable in a connection interface with a second mating surface of the bone fastener. Systems, spinal implants and methods are disclosed.

20 Claims, 16 Drawing Sheets

(56) References Cited

U.S. PATENT DOCUMENTS

| | | | |
|---|---|---|---|
| 2013/0282019 A1* | 10/2013 | Bouliane | A61B 17/8888 |
| | | | 606/104 |
| 2015/0105833 A1* | 4/2015 | Simpson | A61B 17/8875 |
| | | | 606/86 R |
| 2015/0282855 A1* | 10/2015 | Bess | A61B 17/7082 |
| | | | 606/86 A |
| 2016/0262809 A1 | 9/2016 | May et al. | |
| 2016/0296266 A1* | 10/2016 | Chandanson | B25B 23/0035 |
| 2017/0333093 A1* | 11/2017 | Krier | A61B 17/7082 |
| 2018/0116814 A1* | 5/2018 | Sullivan | A61B 17/864 |
| 2018/0177536 A1 | 6/2018 | Divincenzo et al. | |
| 2018/0214190 A1 | 8/2018 | Erramilli et al. | |
| 2019/0029737 A1* | 1/2019 | Wall | A61B 17/8886 |

\* cited by examiner

SPINAL IMPLANT SYSTEM AND METHOD

TECHNICAL FIELD

The present disclosure generally relates to medical devices for the treatment of musculoskeletal disorders, and more particularly to a surgical system and a method for treating a sacro-iliac joint.

BACKGROUND

The sacro-iliac joint is a diarthrodial joint that joins the sacrum to the ilium bones of the pelvis. In the sacro-iliac joint, the sacral surface has hyaline cartilage that moves against fibrocartilage of the iliac surface. The spinal column is configured so that the weight of an upper body rests on the sacro-iliac joints at the juncture of the sacrum and ilia. Stress placed on the sacro-iliac joints in an upright position of the body makes the lower back susceptible to injury.

Disorders of the sacro-iliac joint can cause low back and radiating buttock and leg pain in patients suffering from degeneration and laxity of the sacro-iliac joint. In some cases, the sacro-iliac joint can undergo dehydration and destabilization, similar to other cartilaginous joints, which causes significant pain. The sacro-iliac joint is also susceptible to trauma and degeneration, from fracture and instability. It is estimated that disorders of the sacro-iliac joint are a source of pain for millions of people suffering from back and radicular symptoms.

Non-surgical treatments, such as medication, injection, mobilization, rehabilitation and exercise can be effective, however, may fail to relieve the symptoms associated with these disorders. Surgical treatment of these disorders can include the use of implants for fusion and/or fixation to provide stability to a treated region. During surgical treatment, surgical instruments can be used to deliver the implants to a surgical site for fixation with bone to immobilize a joint. This disclosure describes an improvement over these prior technologies.

SUMMARY

In one embodiment, a surgical instrument is provided. The surgical instrument comprises an outer sleeve including an inner surface that defines a cavity. An inner shaft is fixed with the outer sleeve and extends within the cavity. The inner shaft includes a drive engageable in a torque interface with a first mating surface of a bone fastener. An inner sleeve is disposed between the inner shaft and the outer sleeve. The inner sleeve is axially fixed and rotatable relative to the outer sleeve. The inner sleeve includes an element connectable in a connection interface with a second mating surface of the bone fastener. In some embodiments, systems, spinal implants and methods are disclosed.

In one embodiment, the surgical instrument includes an outer sleeve including an inner surface that defines an axial cavity. An inner shaft is fixed with the outer sleeve and extends within the cavity. The inner shaft includes a hexalobular drive tip engageable in a torque interface with a hexalobular socket of a bone fastener. An inner sleeve is disposed between the inner shaft and the outer sleeve in a relative coaxial orientation. The inner sleeve is axially fixed and rotatable relative to the outer sleeve. The inner sleeve includes a proximal end having a rotatable actuator and a threaded tip connectable in a connection interface with an inner threaded surface of the bone fastener.

In one embodiment, a spinal implant system is provided. The spinal implant system comprises a surgical instrument including an outer sleeve, an inner shaft fixed with the outer sleeve, and an inner sleeve. The inner shaft includes a drive and the inner sleeve is rotatable relative to the outer sleeve and includes an element. A sacro-iliac bone screw has an inner surface and an outer threaded surface. The inner surface includes a socket engageable with the drive in a torque interface and an inner threaded surface connectable with the element in a connection interface. A guide member includes an inner surface that defines a cavity configured for disposal of the outer sleeve and an image guide is oriented relative to a sensor to communicate a signal representative of a position of the guide member.

BRIEF DESCRIPTION OF THE DRAWINGS

The present disclosure will become more readily apparent from the specific description accompanied by the following drawings, in which.

DETAILED DESCRIPTION

Figure 1:
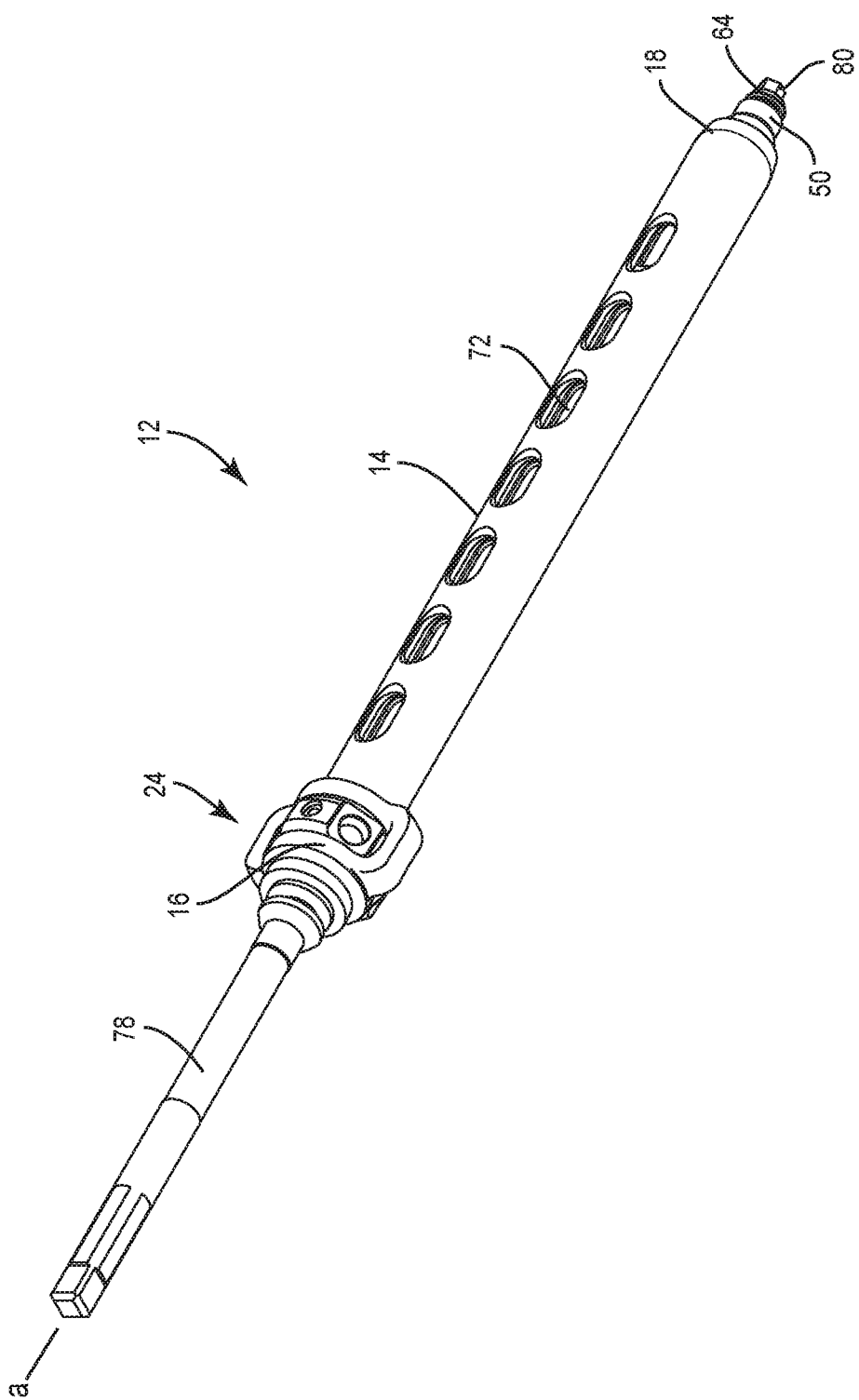
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine. In some embodiments, the surgical system and methods disclosed provide stability and maintain structural integrity while reducing stress on a sacro-iliac (SI) joint. In some embodiments, the present disclosure may be employed to treat musculoskeletal disorders including SI dysfunction or syndrome, dehydration, destabilization and/or laxity.

In some embodiments, the present surgical system comprises a surgical instrument that includes a screw driver engageable with a SI implant having a fully threaded and cannulated body. In some embodiments, the SI implant includes a body that is fenestrated to enhance SI joint fusion. In some embodiments, the driver includes an outer sleeve and inner shaft that are configured as drive and guidance components. In some embodiments, the driver includes an inner sleeve configured with a screw to retain the bone fastener with the driver. In some embodiments, the inner shaft, inner sleeve and outer sleeve are co-axial to facilitate axial translation of the inner sleeve. In some embodiments, the driver includes an inner sleeve and a knob that do not translate axially. In some embodiments, the driver includes a tip that is tapered to allow the SI implant to be sunk deeper into bone.

In some embodiments, the present surgical system comprises a surgical instrument that includes a SI implant driver guidable through an end effector of a robotic arm for guide-wireless screw insertion. In some embodiments, the present surgical system comprises a SI implant driver, a robot arm end effector and a SI cannulated bone screw having a fully threaded body that is fenestrated to enhance SI joint fusion. In some embodiments, the SI implant driver is configured to rotate within an inside diameter of a robotic arm guide without becoming disengaged therefrom. In some embodiments, the SI implant driver includes an inner sleeve and a knob that do not translate axially. In some embodiments, the SI implant driver includes a hex shaped drive that engages a hex shaped socket of a SI implant and is then threaded onto the driver. In some embodiments, the drive engages the socket prior to threading of the components. In some embodiments, the SI implant driver includes a tapered tip, which allows the SI implant to be sunk deeper into bone without bottoming out on the driver. In some embodiments, this configuration allows the SI implant driver to drive the SI implant at extreme angles to the bone surface and enables a sub-flush engagement of the surfaces.

In some embodiments, the present surgical system comprises a surgical instrument that includes a surgical SI bone tap guidable through an end effector of a robotic arm. In some embodiments, the present surgical system comprises a surgical instrument that includes a surgical SI cannula guidable through an end effector of a robotic arm. In some embodiments, the surgical SI bone tap has a larger outside diameter and a fully threaded outer body. In some embodiments, the surgical SI cannula has a larger inner diameter to accommodate the surgical SI bone tap. In some embodiments, the surgical SI cannula is configured as a tissue protector for the surgical SI bone tap.

In some embodiments, the driver includes a knob that serves as a visual indicator of whether or not the driver is fully disengaged from an implant. In some embodiments, the screw driver is employed with robotic guidance and provides indicia of the driver being fully unthreaded from an implant. In some embodiments, the screw driver provides visual indicia that the screw driver is unthreaded from the implant in a minimally invasive surgical procedure. For example, the screw driver provides visual indicia whether the screw driver is or is not engaged.

In some embodiments, the present surgical system includes a screw driver including an outer shaft or sleeve having an outside diameter that is slightly larger than a screw spin diameter of a bone screw. This configuration allows the bone screw and the screw driver to pass through the end effector. In some embodiments, the screw driver includes a thumb wheel that is connected to a retention screw that threads into the bone screw.

In some embodiments, the driver includes an inner shaft having a Torx tip configured for engagement with the bone fastener. In some embodiments, upon engagement of the Torx tip with the bone fastener, an actuator, for example, a thumb wheel is actuated to cause an inner sleeve and screw to tighten and pull the bone fastener into engagement with the driver. The outer sleeve is fixed to the inner shaft, for example, by welding.

In some embodiments, the present surgical system comprises a surgical instrument that comprises a screw driver that can be employed with bone fasteners and one or more implant supports for treating a spine. In some embodiments, the present surgical system includes a surgical instrument that can easily connect and disconnect from a bone fastener. In some embodiments, the present surgical system includes a surgical instrument that can be employed with an end effector of a robotic arm to facilitate implantation with the robotic arm. In some embodiments, the surgical instrument is guided through the end effector for a guide-wireless screw insertion. In some embodiments, the surgical instrument comprises a robot screw driver employed with robotic and/or navigation guidance, which may include an image guide.

In some embodiments, the present surgical system includes a screw driver including an outer shaft or sleeve having an outside diameter that is slightly larger than a screw spin diameter of a bone screw. This configuration allows the bone screw and the screw driver to pass through the end effector. In some embodiments, the screw driver includes a thumb wheel that is connected to a retention screw that threads into the bone screw.

In some embodiments, the surgical system of the present disclosure comprises a cannulated SI implant having a fully threaded body that is fenestrated to enhance SI joint fusion and to provide fixation of large bones and large bone fragments of the pelvis. In some embodiments, the present system includes one or more spinal constructs having one or more SI implants that are provided having various lengths to accommodate patient anatomy. In some embodiments, the SI implant is utilized with an SI joint fusion procedure for conditions including SI joint disruptions and degenerative sacroiliitis.

In some embodiments, the SI implant includes a fully threaded body having a thread form that extends an entire length of the body from a proximal end to a tip of a distal end. In some embodiments, the SI implant is cannulated and fenestrated to allow for bony ingrowth and for bone graft material to be packed inside the SI implant and on or about one or more components of the spinal construct to promote fusion across the SI joint. In some embodiments, the SI implant includes a recess on a proximal end to facilitate a threaded engagement with a surgical instrument, such as, for example, an inserter. In some embodiments, the inserter is configured for manual insertion, assisted with navigation and/or with a powered driver.

In some embodiments, the present surgical system includes a tapered, fully threaded, cannulated, fenestrated SI implant for stabilization and fusion of the SI joint. In some embodiments, the present surgical system is employed with a method for treating low back pain attributed to the SI joint. In some embodiments, the present surgical system includes a threaded SI implant that is cannulated, fenestrated, and designed to enhance SI joint fusion and provide fixation of large bones and large bone fragments of the pelvis. In some embodiments, the SI implant includes a distal tip having a blunt configuration. In some embodiments, the SI implant includes a bore having a threaded portion. In some embodiments, the threaded portion is configured to facilitate a revision procedure. In some embodiments, the bore includes a connection portion and/or a torque portion.

In some embodiments, the present system is employed with a method used with surgical navigation, for example, fluoroscope or image guidance. In some embodiments, the presently disclosed system and/or method reduce operating time for a surgical procedure and reduce radiation exposure due to fluoroscope or image guidance, for example, by eliminating procedural steps and patient repositioning by implanting system components in one body position.

In some embodiments, the present system is employed with a method for treating an SI joint, which includes the step of identifying a posterior superior iliac spine on a patient that is positioned in a prone position on an operating table. In some embodiments, the step of identifying includes using the posterior superior iliac spine as a landmark for making an incision. In some embodiments, identification of the posterior superior iliac spine limits vascular and muscular disruption from a surgical approach. In some embodiments, the method includes the step of establishing a trajectory path using fluoroscopy and a guide wire inserted into the posterior superior iliac spine, for example, on an iliac side of an SI joint. In some embodiments, bone graft material, for example, autograft and/or allograft is inserted into the SI joint space to create a bony contact between the iliac and sacrum sides. In some embodiments, the bone graft material is inserted into a cannula of a screw.

In some embodiments, the present system includes an SI fixation screw attached to a surgical driver. In some embodiments, the SI fixation screw is employed with a method for treating an SI joint, which includes the step of applying a downward force and driving the screw through the ilium, through the graft material and into the sacrum following a path created by a reamer until the screw is flush with the ilium and docked into the sacrum. In some embodiments, screw placement is confirmed with fluoroscopy and/or image guidance and the incision is closed. In some embodiments, the present system is employed with a method for screw removal from the SI joint fusion. In some embodiments, the method includes the step of providing an implant inserter configured to attach to the screw. In some embodiments, the method includes the step of exposing an iliac side of the SI joint of a patient who underwent a SI fusion procedure. In some embodiments, a tube can be placed over the incision site. In some embodiments the dorsal aspect of the screw is positively identified. In some embodiments, the dorsal aspect of the screw is identified by fluoroscopy and/or image guidance. In some embodiments, the implant inserter is re-attached to the dorsal end of the screw and the screw is removed.

In some embodiments, the present system includes an SI implant and a surgical inserter that employs image guidance, for example, surgical navigation. In some embodiments, the present system includes an SI implant and a surgical inserter that selectively, precisely and/or accurately connects the SI implant with the surgical inserter such that the SI implant extends a selected distance from the surgical inserter in connection with surgical navigation. In some embodiments, the SI implant extends a selected distance from the surgical inserter within an accuracy and/or tolerance of ±1.0 millimeter (mm). In some embodiments, the SI implant extends a selected distance from the surgical inserter, and is connected at a first component interface having a selected distance within an accuracy and/or tolerance of ±0.5 mm. In some embodiments, the component interface has a selected distance within an accuracy and/or tolerance of ±0.2 mm. In some embodiments, the component interface includes a threaded pocket of the SI implant. In some embodiments, the surgical inserter includes a floating, relative rotating sleeve disposed along a shaft of a driver. In some embodiments, the sleeve comprises a portion of the component interface to selectively locate the SI implant at the end of the driver while allowing the driver to pass through the sleeve and engage a second component interface of the SI implant. In some embodiments, the SI implant extends a selected distance from and is fixed with the surgical inserter in connection with image guidance to provide position of the SI implant with tissue for a reliable explant strategy, which may include locating the SI implant with tissue and explant of the SI implant.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-20, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant at a surgical site of a patient, for example, regions of a spine including vertebrae, iliac bone and/or articular surfaces of the SI joint. In some embodiments, the components of spinal implant system 10 are employed to stabilize and maintain structural integrity while reducing stress on the SI joint and/or portions of the anatomy adjacent the SI joint. In some embodiments, spinal implant system 10 is configured to treat SI joint disorders including those caused by degeneration or trauma. In some embodiments, spinal implant system 10 is adapted to immobilize opposing naturally separated surfaces of a SI joint. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine, and/or iliac bone.

Spinal implant system 10 includes a surgical instrument, such as, for example, a driver 12. Driver 12 can be employed with an end effector 200 (FIG. 12) of a robotic arm R (FIG. 19) to facilitate implantation with robotic arm R. Driver 12 is guided through end effector 200 for guide-wireless insertion of a spinal implant, such as, for example, a bone fastener 100, as described herein.

Driver 12 includes a member, for example, an outer tubular sleeve 14. Outer sleeve 14 extends between a proximal end 16 and a distal end 18. Outer sleeve 14 defines a longitudinal axis a. In some embodiments, outer sleeve 14 may have various configurations including, for example, round, oval, polygonal, irregular, consistent, variable, uniform and non-uniform. Outer sleeve 14 includes a diameter D1. In some embodiments, diameter D1 is slightly larger than a proximal end diameter D2 of bone fastener 100. This configuration allows bone fastener 100 and driver 12 to pass through end effector 200 of robotic arm R, as described herein.

Figure 9:
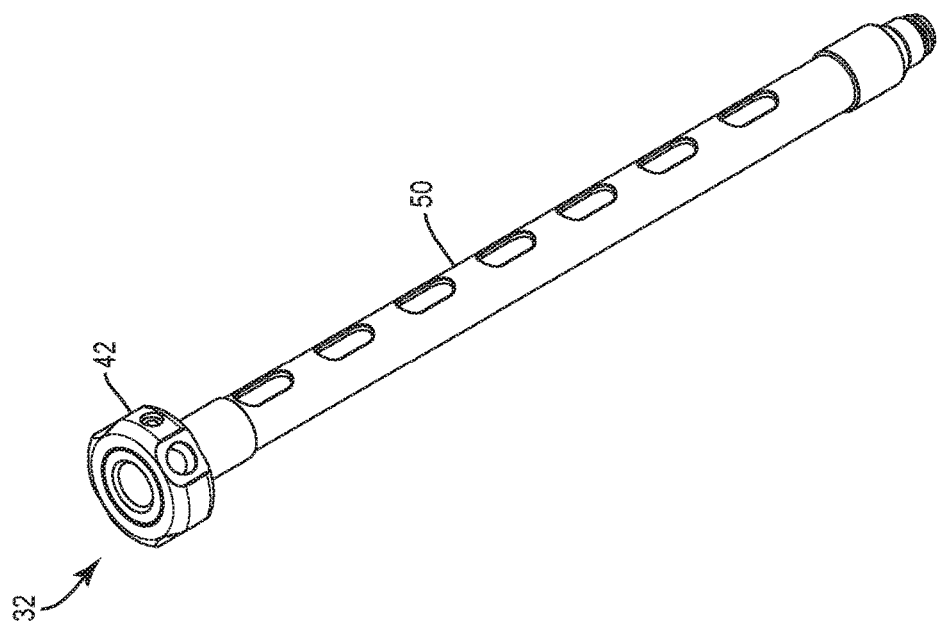
FIG. 9 is a perspective view of the components shown in FIG. 8.
Figure 8:
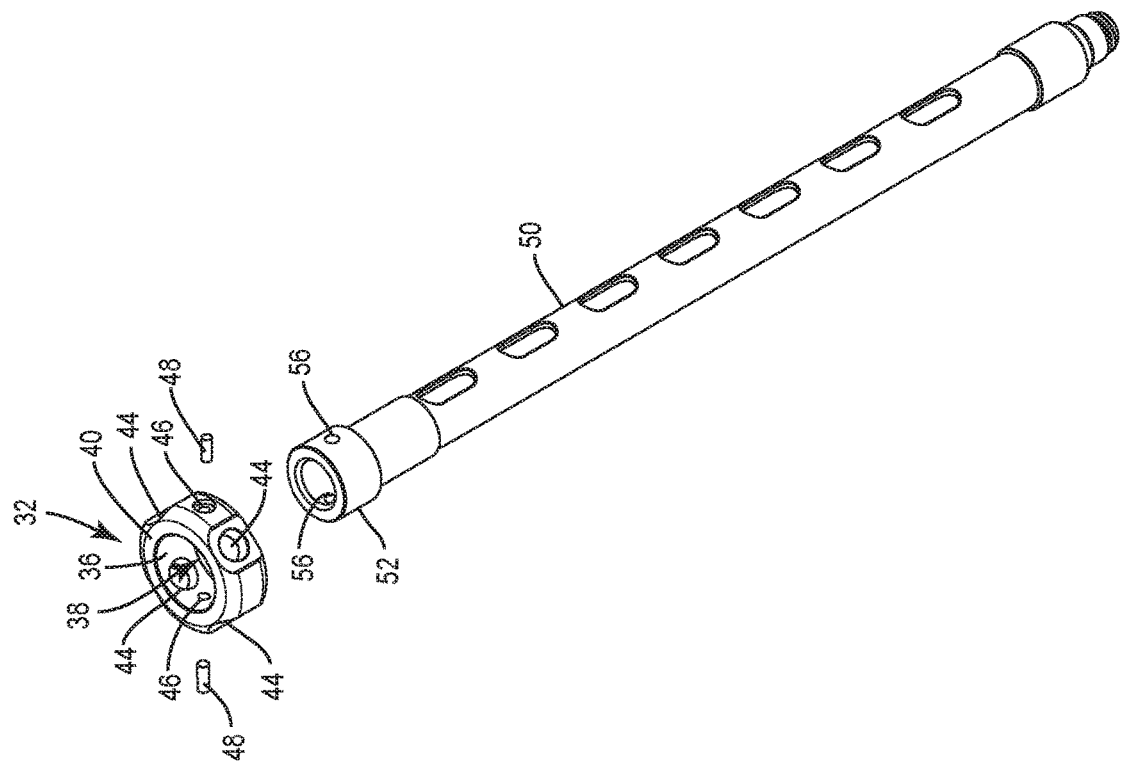
FIG. 8 is a break away perspective view of components of the system shown in FIG. 7.
Figure 11:
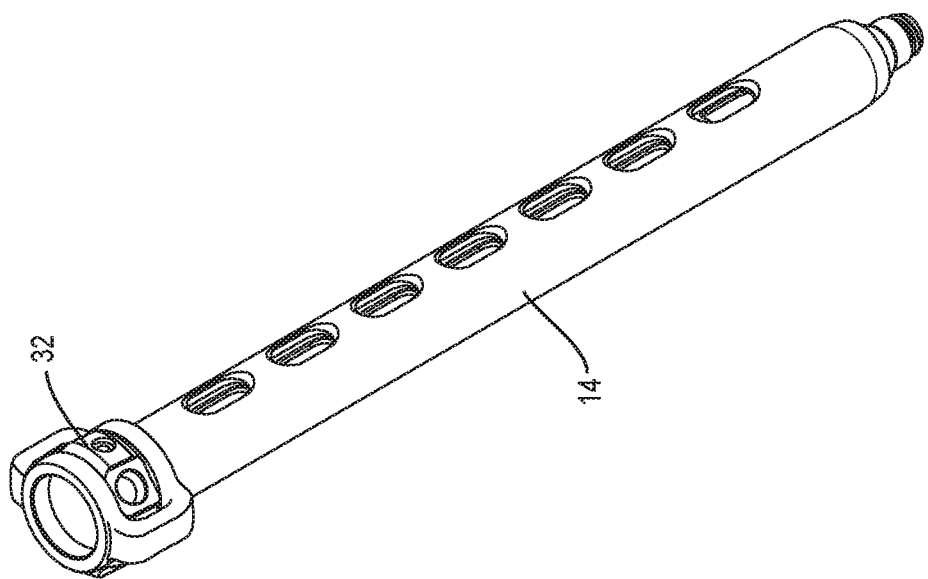
FIG. 11 is a perspective view of the components shown in FIG. 10.
Figure 10:
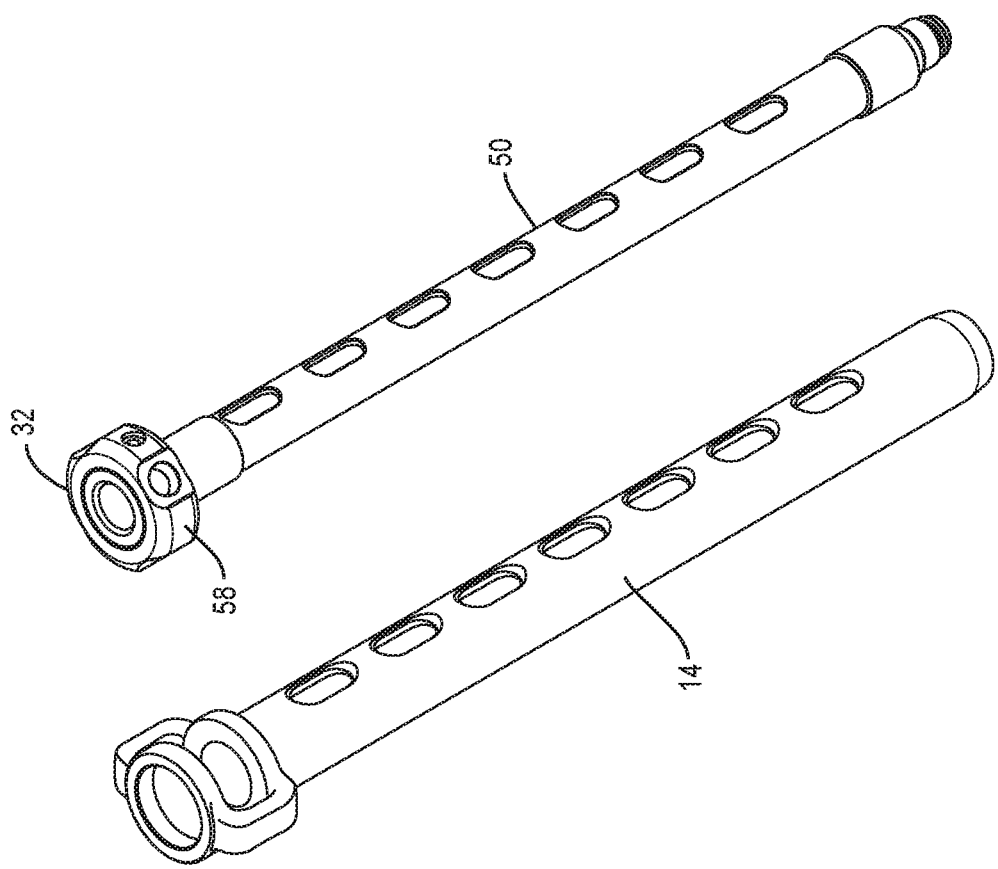
FIG. 10 is a perspective view of components of the system shown in FIG. 7.
Figure 12:
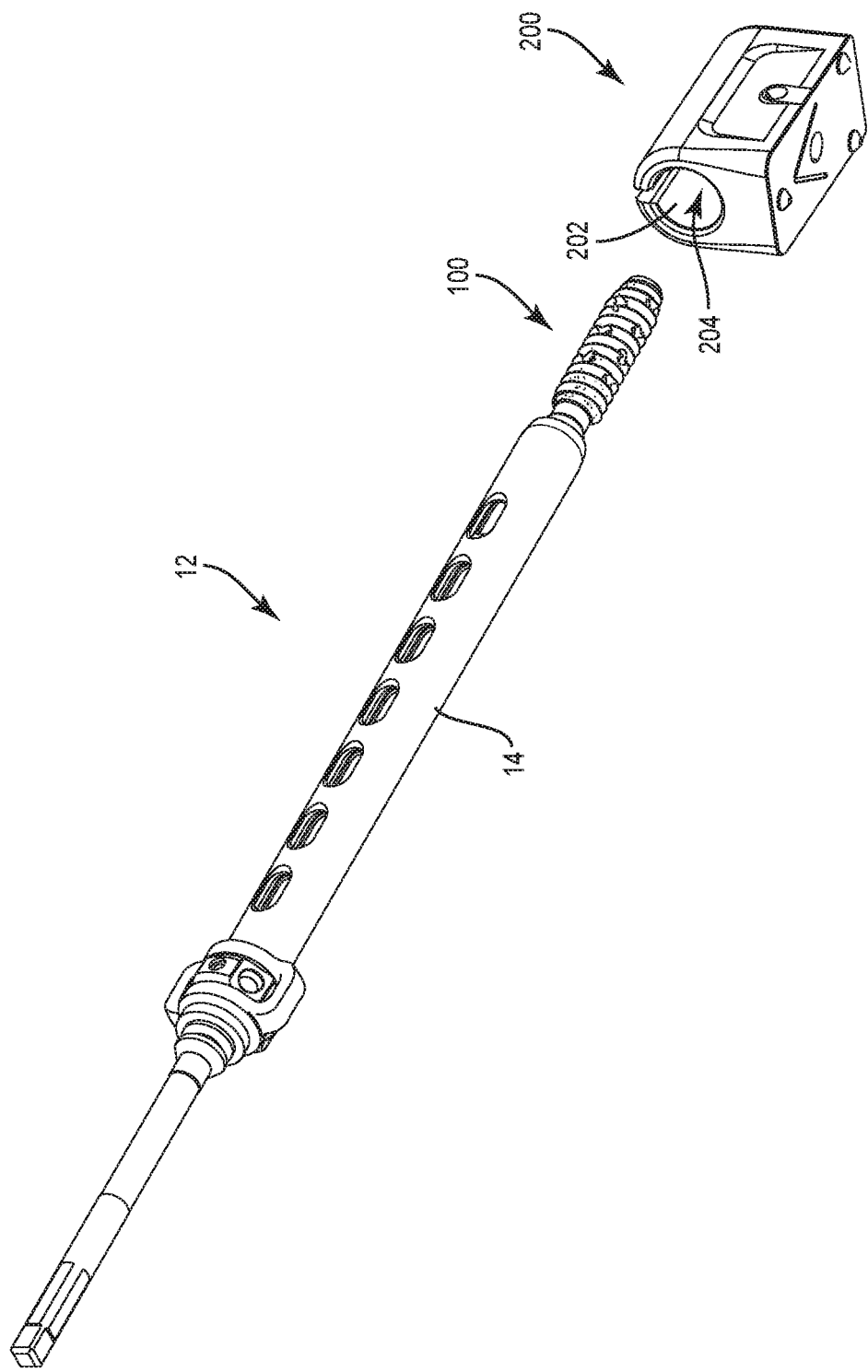
FIG. 12 is a perspective view of components of one embodiment of a surgical system in accordance with the principles of the present disclosure.
Figure 13:
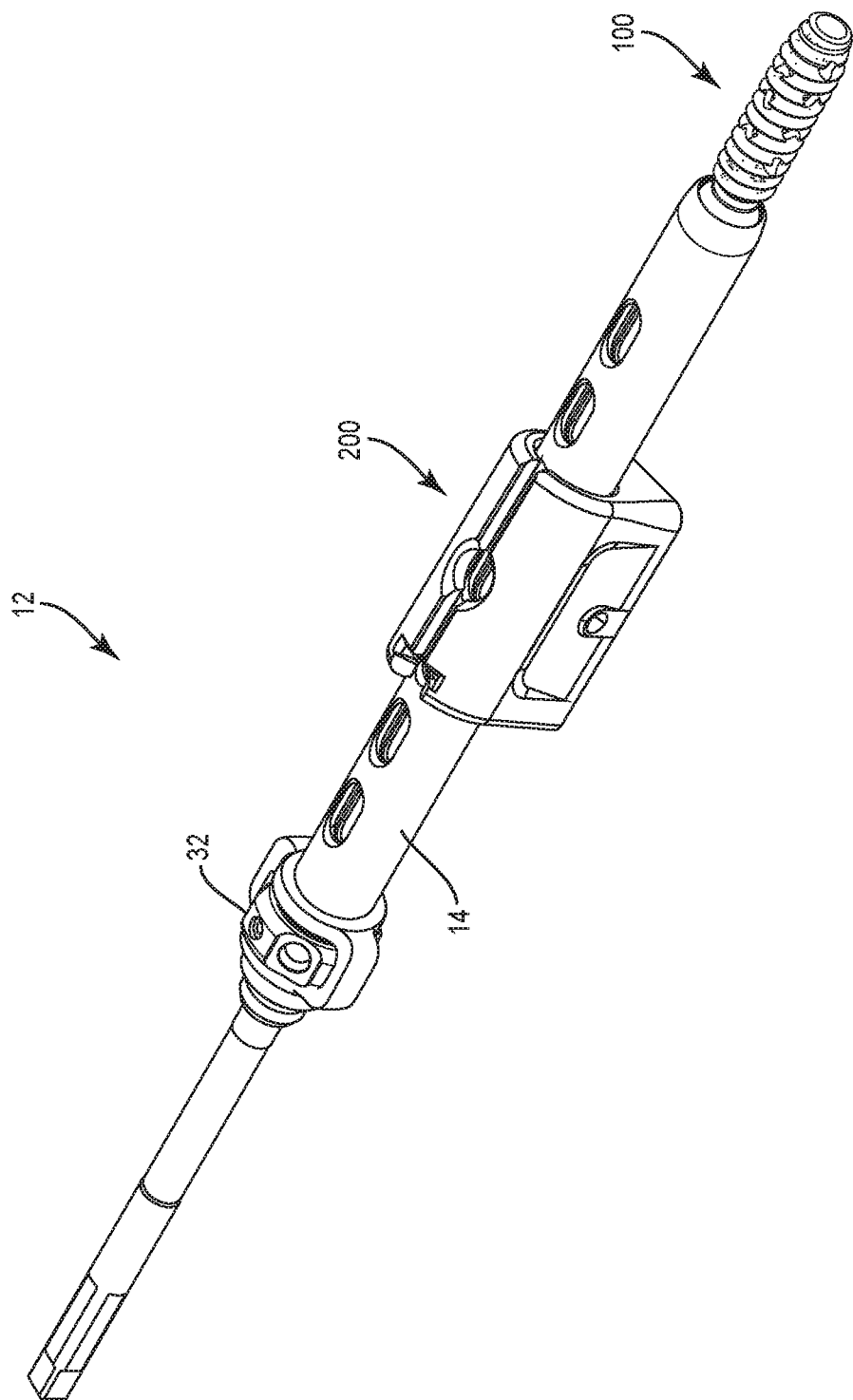
FIG. 13 is a perspective view of the components shown in FIG. 12.

Outer sleeve 14 includes a surface 20 that defines an axial cavity 22. Cavity 22 is configured for disposal of an inner sleeve 50 and an inner shaft 72, as described herein. Outer sleeve 14 includes a collar body 24 having a surface 26. Surface 26 defines a cavity 28. Body 24 includes bifurcated arms 30 disposed about cavity 28 to facilitate disposal and access to an actuator, for example, a thumb wheel 32 therein. Body 24 includes opening 34 disposed at end 16. Opening 34 is in communication with cavity 28 and in alignment with cavity 22 to facilitate insertion of inner shaft 72 into end 16, through wheel 32 and into cavity 22 for assembly, as described herein. Wheel 32 is axially fixed and rotatable relative to outer sleeve 14 and is configured to be integrally connected with inner sleeve 50 such that wheel 32 and inner sleeve 50 do not translate axially. In some embodiments, wheel 32 can be monolithically formed with inner sleeve 50. Wheel 32 includes a surface 36 that defines a cavity 38. Cavity 38 is configured for disposal of a correspondingly shaped portion of inner sleeve 50, as shown in FIGS. 8 and 9.

Wheel 32 includes a wall 40 having a surface 42. Surface 42 defines a plurality of openings 44 and opposing holes 46. Holes 46 are configured for engagement with pins 48 to integrally connect wheel 32 with inner sleeve 50.

Figure 7:
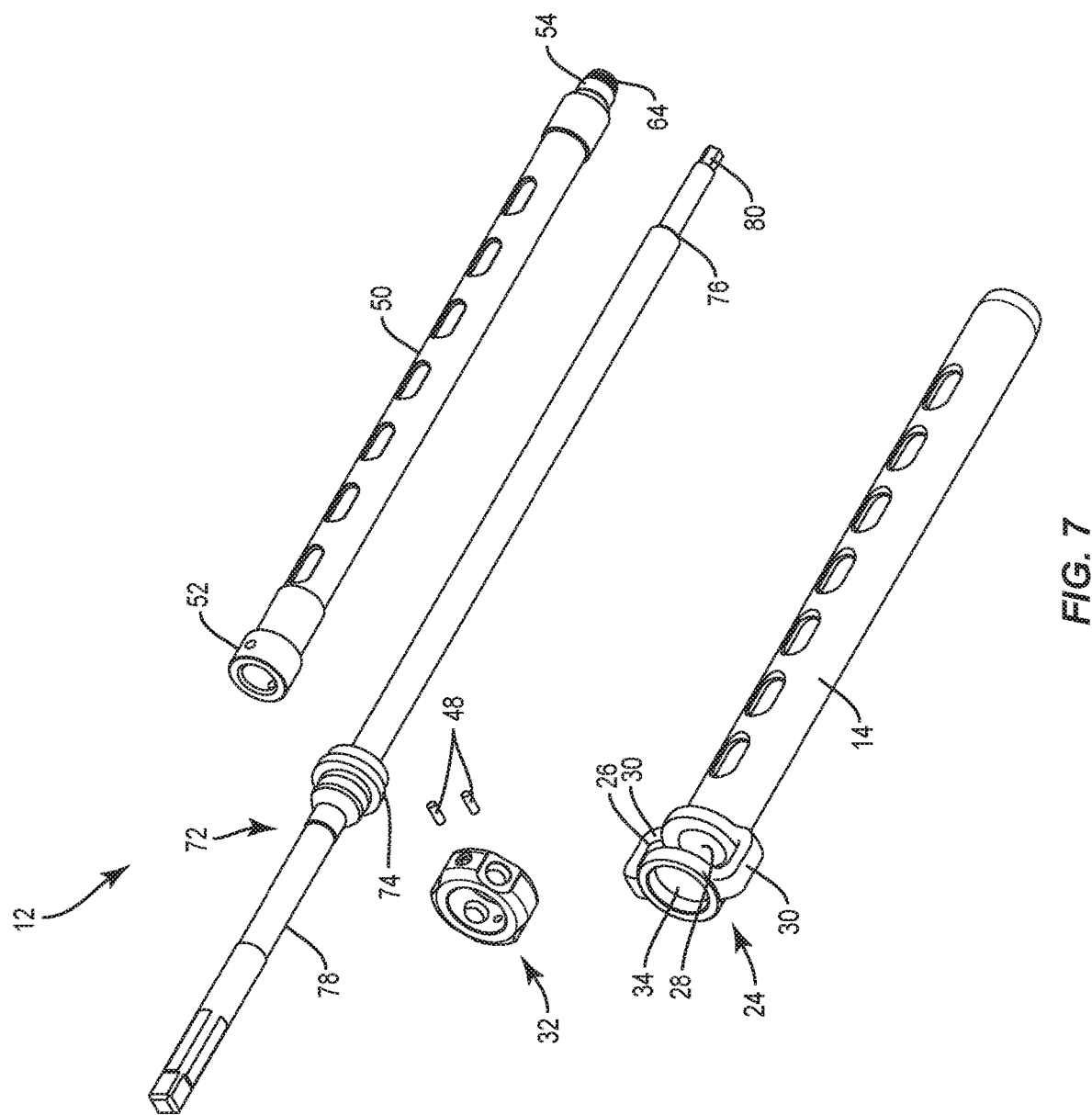
FIG. 7 is a perspective view of the components shown in FIG. 3 with parts separated.

Inner sleeve 50 is configured for disposal between inner shaft 72 and outer sleeve 14 and is axially fixed and rotatable relative to outer sleeve 14. Inner sleeve 50 extends between a proximal end 52 and a distal end 54, as shown in FIG. 7. End 52 is connected to wheel 32. Wheel 32 is integrally connected with inner sleeve 50. End 52 includes openings 56 that are each configured to engage with a pin 48 to connect wheel 32 to inner sleeve 50. Wheel 32 actuates rotation of inner sleeve 50 relative to outer sleeve 14. In some embodiments, surface 36 defines a circular cross section of cavity 38 for a mating engagement with correspondingly shaped end 52 of inner sleeve 50. In some embodiments, cavity 38 includes various configurations, such as, for example, circular, hexalobe, cruciform, phillips, square, polygonal, star cross sectional configuration for a mating engagement with correspondingly shaped portion of inner sleeve 50. In some embodiments, wheel 32 includes a surface 58 configured to facilitate gripping of wheel 32, for example, an indented surface.

As shown in FIGS. 8-11, assembly of outer sleeve 14 with inner sleeve 50 and wheel 32 includes inserting wheel 32 through arms 30 and into cavity 28. Inner sleeve 50 is then translated through cavity 22 of outer sleeve 14. End 52 of inner sleeve 50 is translated into cavity 38 of wheel 32 and each pin 48 is inserted into each hole 46 and opening 56. Pins 48 resist and/or prevent disengagement of inner sleeve 50 from wheel 32.

Inner sleeve 50 includes an inner surface 60. Surface 60 defines an axial channel 62 configured for moveable disposal of inner shaft 72, as described herein. Channel 62 extends coaxial with cavity 22. In some embodiments, channel 62 is disposed at alternate orientations relative to axis a, for example, at transverse, perpendicular and/or other angular orientations such as acute or obtuse, and/or may be offset or staggered. End 54 of inner sleeve 50 includes an element, for example, a screw 64. Screw 64 includes a threaded outer surface 66. Threaded outer surface 66 is disposed adjacent a distal most position of inner sleeve 50. Threaded outer surface 66 is connectable or engageable in a connection interface with a mating surface, for example, an inner threaded surface 102 of bone fastener 100 to retain and/or draw bone fastener 100 into engagement with driver 12, as described herein.

Figure 6:
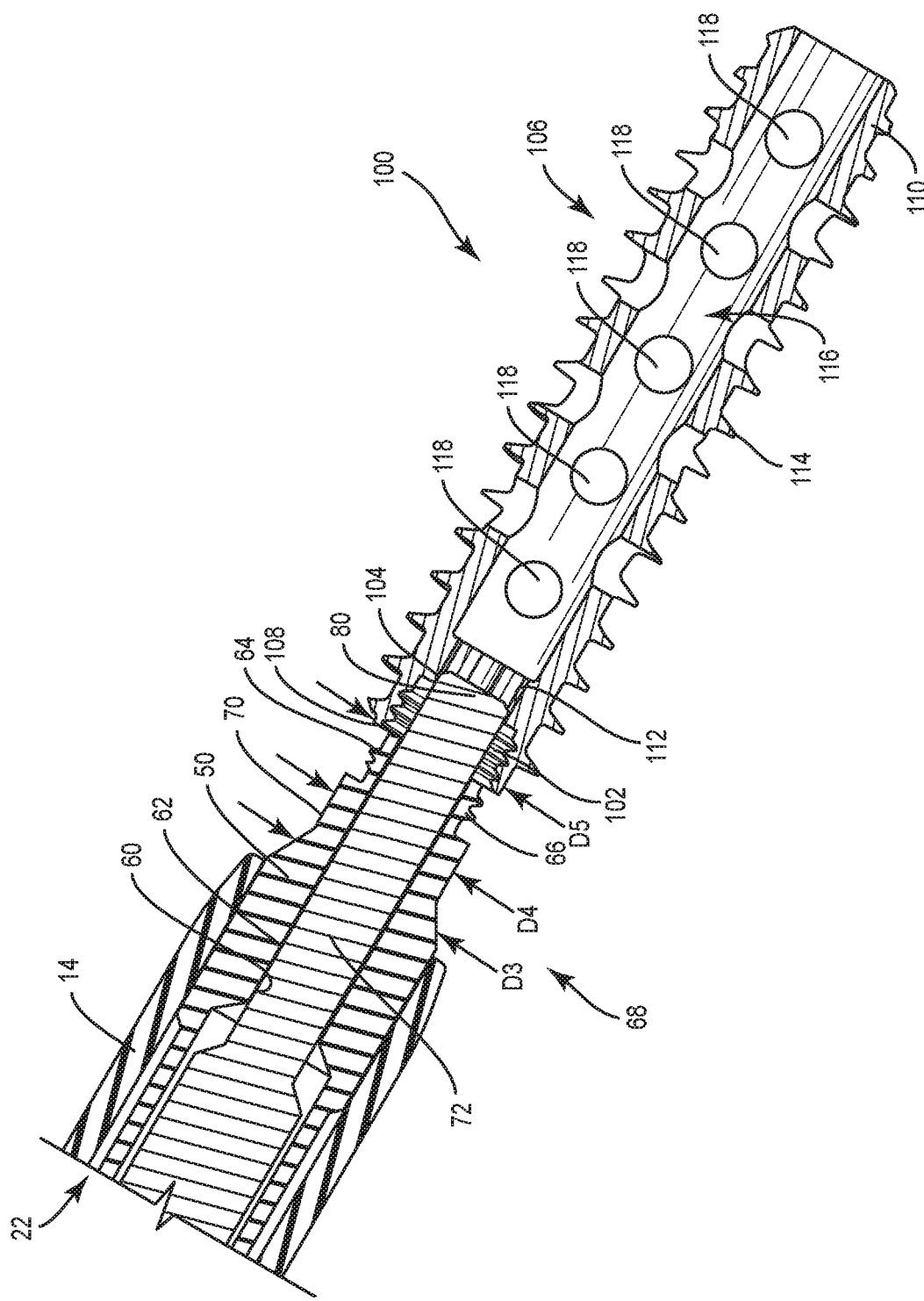
FIG. 6 is a break away view of the components shown in FIG. 5.

Distal end 54 of inner sleeve 50 includes a tapered tip or portion 68 that extends to screw 64. Tapered portion 68 is configured such that bone fastener 100 can be implanted with tissue below an outer surface of bone, sunk into bone and/or disposed in a sub-flush orientation with and into bone, without bottoming out a distal end of driver 12 with adjacent bone surfaces. Tapered portion 68 includes a decreasing diameter D3 and an axial portion 70 have a uniform diameter D4, as shown in FIG. 6. Diameter D4 has a diameter that is substantially equal to a minor diameter D5 of bone fastener 100.

Figure 14:
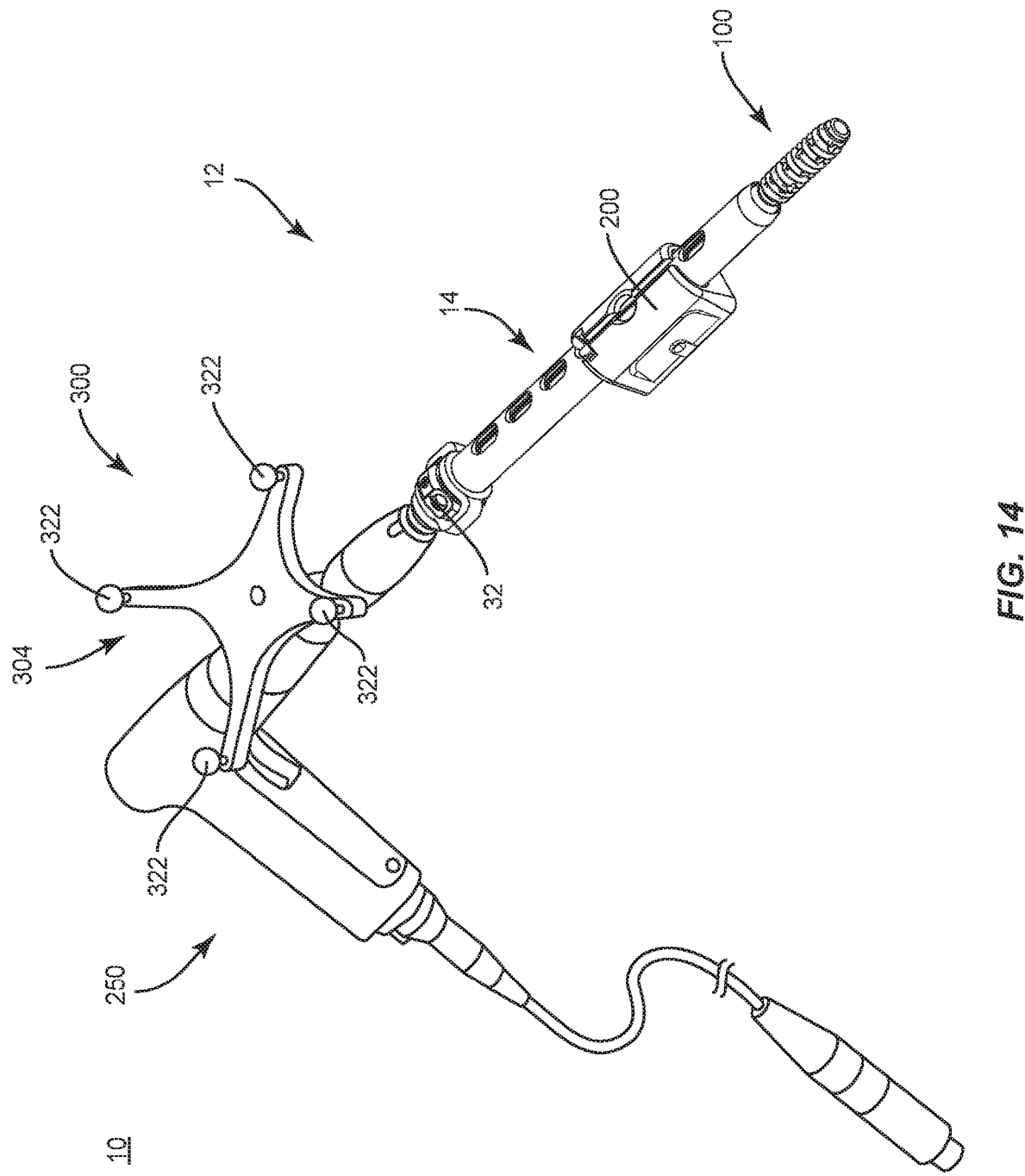
FIG. 14 is a perspective view of components of one embodiment of a surgical system in accordance with the principles of the present disclosure.

Inner shaft 72 extends between an end 74 and an end 76. Inner shaft 72 extends within cavity 22 of outer sleeve 14 and is disposable with channel 62 of inner sleeve 50, as described herein. Inner shaft 72 is fixed with outer sleeve 14 such that rotation of inner shaft 72 causes simultaneous rotation of outer sleeve 14. In some embodiments, inner shaft 72 is welded with outer sleeve 14. Inner shaft 72 rotates independently from inner sleeve 50. In some embodiments, inner shaft 72 includes a portion 78 configured to facilitate connection of driver 12 with a surgical instrument, for example, an actuator/drill 250, as shown in FIG. 14. In some embodiments, inner shaft 72 includes quick connect surfaces or keyed geometry, such as, for example, triangle, hex, square or hexalobe to facilitate connection with actuator 250.

End 76 of inner shaft 72 includes a distal tip, for example, drive 80, as shown in FIG. 1. Drive 80 is integrally connected or monolithically formed with inner shaft 72. This configuration facilitates control of tolerances to optimize accuracy of the connection of inner shaft 72 with bone fastener 100. Drive 80 and screw 64 of inner sleeve 50 are disposed in a serial orientation. Drive 80 is engageable in a torque interface with a spinal implant, for example, bone fastener 100. For example, drive 80 fits with and is engageable with a mating surface, for example, a socket 104 of bone fastener 100, as shown in FIG. 6. Rotation of inner shaft 72 simultaneously rotates drive 80 to drive, torque, insert or otherwise connect bone fastener 100 with tissue, as described herein. Drive 80 includes a hexalobular geometry and includes a hexalobular cross section for a mating engagement with correspondingly shaped socket 104. In some embodiments, drive 80 can alternatively include a cruciform, phillips, square, hexagonal, polygonal, star cross sectional configuration for disposal of socket 104.

Wheel 32 is inserted laterally through arms 30 and into cavity 28. Inner sleeve 50 is then translated through cavity 22 of outer sleeve 14. End 52 of inner sleeve 50 is translated into cavity 38 of wheel 32 and each pin 48 is inserted into each hole 46 and opening 56. Inner shaft 72 is inserted from end 16, through opening 34, through cavity 38 to provisionally connect wheel 32 with outer sleeve 14. Inner shaft 72 is welded to outer sleeve 14. Inner shaft 72 is disposed with channel 62 of inner sleeve 50. Inner sleeve 50 is rotatable relative to outer sleeve 14 and inner shaft 72. Inner shaft 72 and outer sleeve 14 simultaneously rotate relative to inner sleeve 50.

Bone fastener 100 includes a body 106 that extends between a proximal end 108 and a distal end 110. Body 106 is configured to penetrate tissue, for example, bone. An inner surface 112 disposed at end 108 includes socket 104 that is engageable with drive 80 in a torque interface, and inner threaded surface 102 that is connectable with screw 64 in a connection interface, as described herein. Bone fastener 100 includes an outer threaded surface 114 that is threaded an entire length of body 106.

Bone fastener 100 includes a longitudinal cavity 116 and a plurality of lateral openings, such as fenestrations 118 that are in communication with cavity 116. Bone fastener 100 is cannulated and fenestrated to allow for bony ingrowth and for bone graft material to be packed inside bone fastener 100 to promote fusion across the SI joint. See, for example, a similar bone fastener and its use, as described in U.S. Patent Publication No. 2018/0116814, the entire contents of this reference being incorporated by reference herein.

Figure 2:
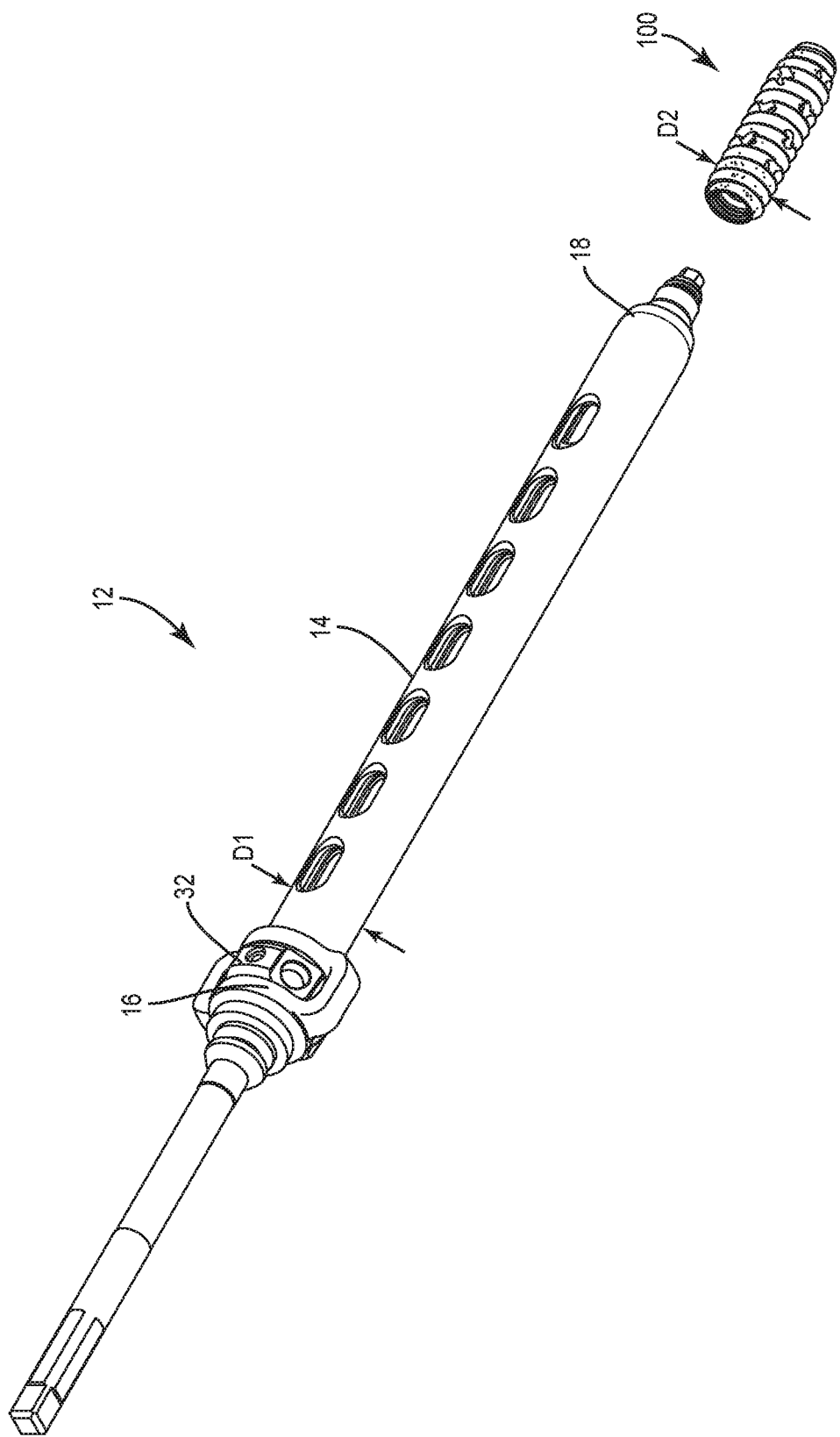
FIG. 2 is a perspective view of components of one embodiment of a surgical system with parts separated in accordance with the principles of the present disclosure.
Figure 3:
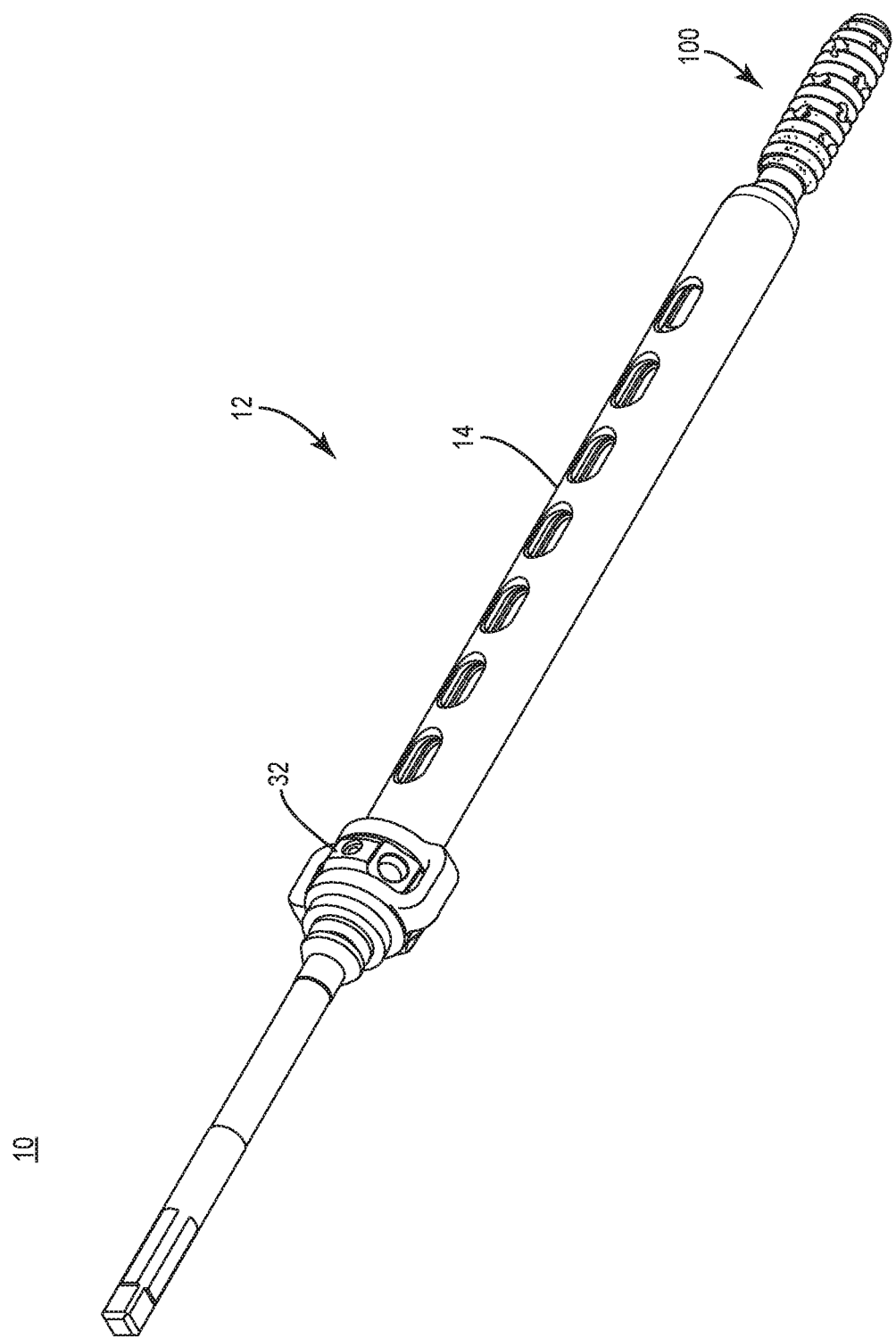
FIG. 3 is a perspective view of the components shown in FIG. 2.
Figure 4:
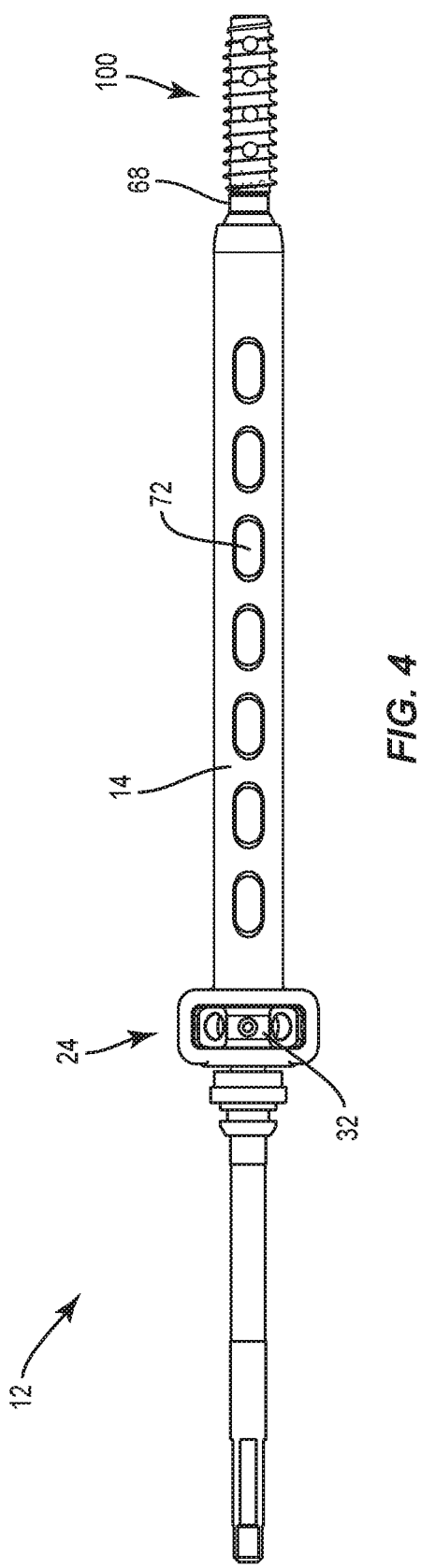
FIG. 4 is a side view of the components shown in FIG. 3.
Figure 5:
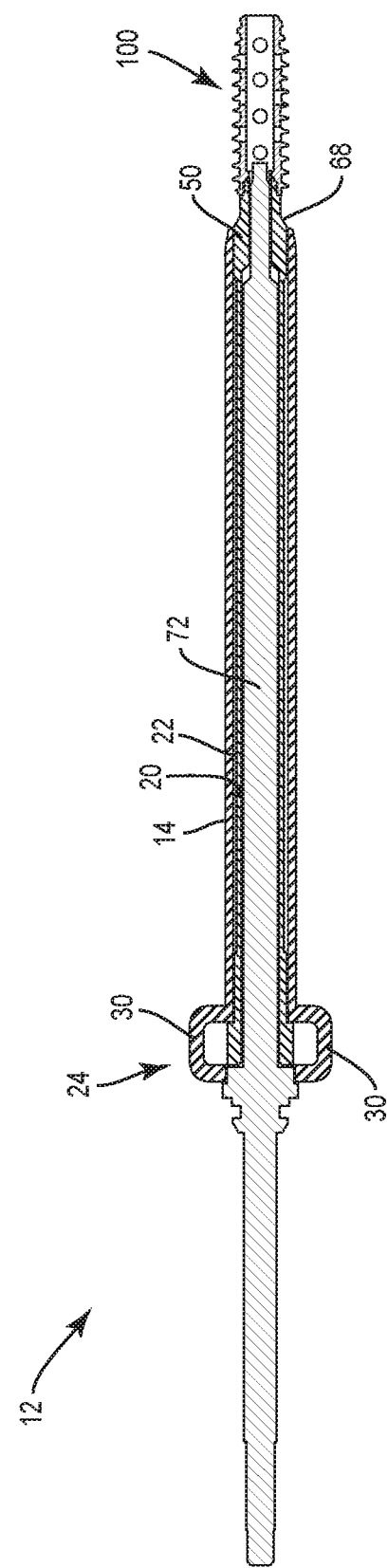
FIG. 5 is a cross section view of the components shown in FIG. 4.

In use, drive 80 is aligned with end 108 of bone fastener 100 for disposal with socket 104 and screw 64 is aligned with inner threaded surface 102, as shown in FIG. 2. Driver 12 is axially translated to connect to bone fastener 100 in a non-locking configuration, as shown in FIG. 6. Drive 80 is engaged with socket 104 and wheel 32 is manipulated for rotation such that inner sleeve 50 rotates screw 64 relative to and independent of outer sleeve 14. Rotation of screw 64 creates a threaded engagement between outer threaded surface 66 of screw 64 and inner threaded surface 102 of bone fastener 100 to retain and/or draw bone fastener 100 into engagement with driver 12 in a locking configuration, as shown in FIG. 5.

Inner shaft 72 with drive 80 is connected with outer sleeve 14, as described herein, and inner shaft 72 and outer sleeve 14 are rotated to drive, torque, insert or otherwise connect bone fastener 100 with adjacent tissue. Screw 64 remains releasably fixed with inner threaded surface 102, independent of inner shaft 72 and outer sleeve 14 rotation and/or engagement or friction with components of spinal implant system 10 as described herein, to resist and/or prevent disengagement or unthreading of screw 64 from inner threaded surface 102. In some embodiments, wheel 32 is manipulated for rotation such that inner sleeve 50 and screw 64 rotate relative to outer sleeve 14, and outer threaded surface 66 disengages with inner threaded surface 102, to place driver 12 in the non-locking configuration, as shown in FIG. 2.

Figure 19:
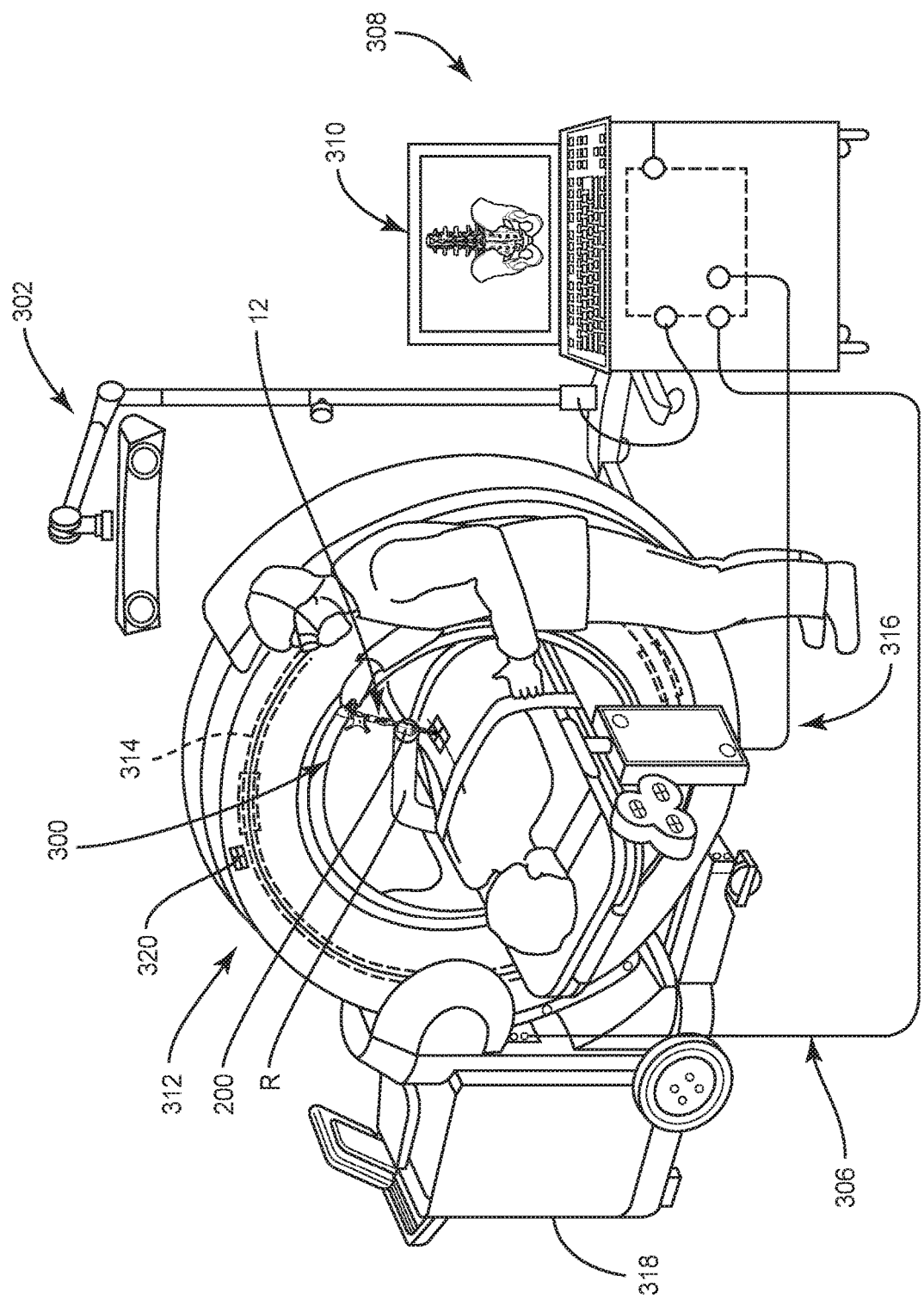
FIG. 19 is a perspective view of components of one embodiment of a surgical system in accordance with the principles of the present disclosure.
Figure 20:
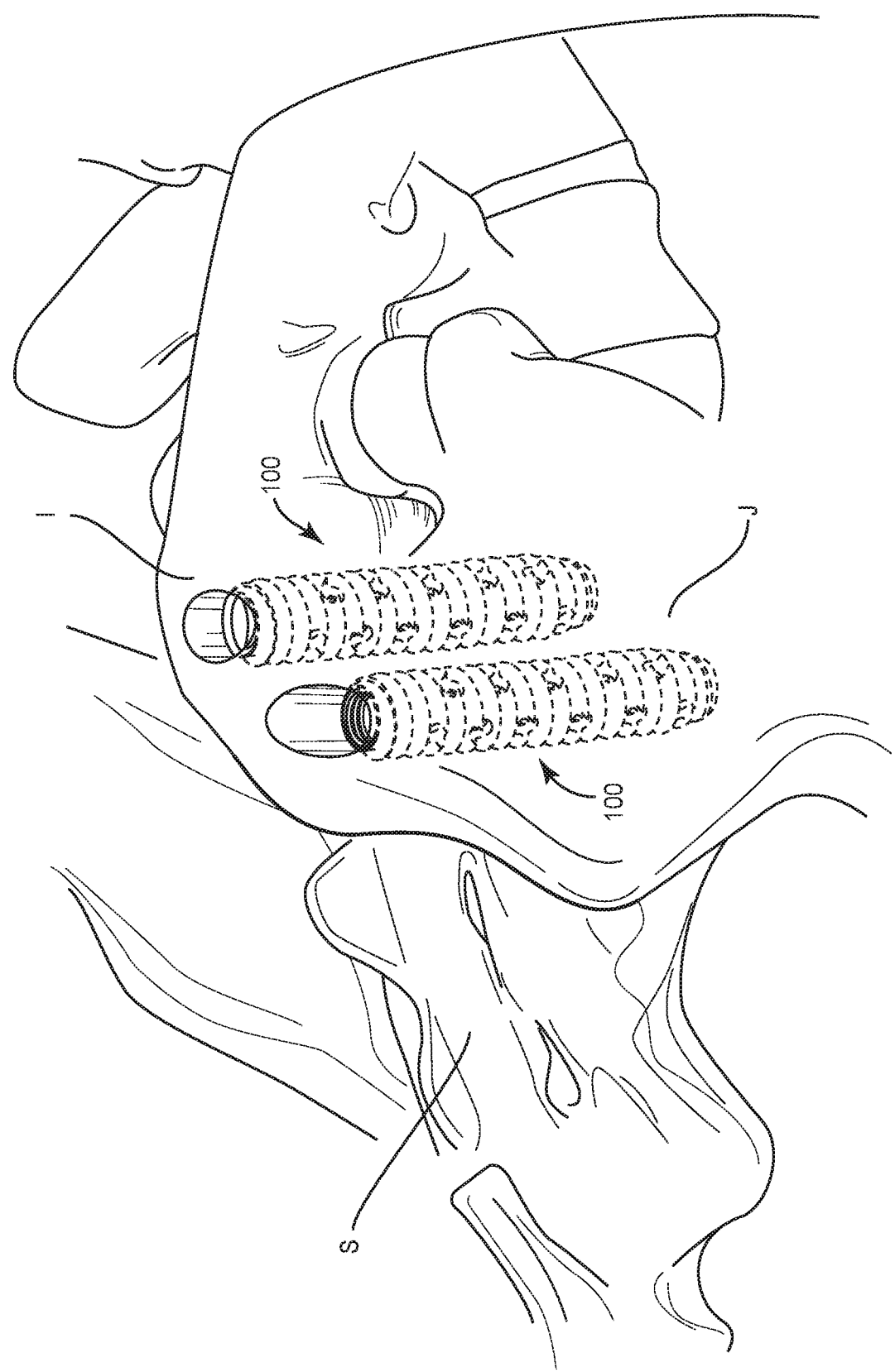
FIG. 20 is a perspective view, in part phantom, of components of the system shown in FIG. 18 disposed with a patient anatomy.

In some embodiments, driver 12 includes a navigation component 300, as shown in FIGS. 14 and 19. Driver 12 is configured for disposal adjacent a surgical site such that navigation component 300 is oriented relative to a sensor array 302 to facilitate communication between navigation component 300 and sensor array 302 during a surgical procedure, as described herein. Navigation component 300 is configured to generate a signal representative of a position of bone fastener 100 relative to driver 12 and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. Navigation component 300 is directly connected to actuator 250, as shown in FIG. 14. In some embodiments, navigation component 300 is connected with portion 78 of inner shaft 72 or outer sleeve 14 via an integral connection, friction fit, pressure fit, interlocking engagement, mating engagement, dovetail connection, clips, barbs, tongue in groove, threaded, magnetic, key/keyslot and/or drill chuck.

Navigation component 300 includes an emitter array 304. Emitter array 304 is configured for generating a signal to sensor array 302 of a surgical navigation system 306, as shown in FIG. 19 and described herein. In some embodiments, the signal generated by emitter array 304 represents a position of bone fastener 100 relative to driver 12 and relative to tissue, for example, bone. In some embodiments, the signal generated by emitter array 304 represents a three dimensional position of bone fastener 100 relative to tissue.

In some embodiments, sensor array 302 receives signals from emitter array 304 to provide a three-dimensional spatial position and/or a trajectory of bone fastener 100 relative to driver 12 and/or tissue. Emitter array 304 communicates with a processor of a computer 308 of surgical navigation system 306 to generate data for display of an image on a monitor 310, as described herein. In some embodiments, sensor array 302 receives signals from emitter array 304 to provide a visual representation of a position of bone fastener 100 relative to driver 12 and/or tissue. See, for example, similar surgical navigation components and their use as described in U.S. Pat. Nos. 6,021,343, 6,725,080, 6,796,988, the entire contents of each of these references being incorporated by reference herein.

Surgical navigation system 306 is configured for acquiring and displaying medical imaging, for example, x-ray images appropriate for a given surgical procedure. In some embodiments, pre-acquired images of a patient are collected. In some embodiments, surgical navigation system 306 can include an O-arm® imaging device 312 sold by Medtronic Navigation, Inc. having a place of business in Louisville, Colo., USA. Imaging device 312 may have a generally annular gantry housing that encloses an image capturing portion 314.

In some embodiments, image capturing portion 314 may include an x-ray source or emission portion and an x-ray receiving or image receiving portion located generally or as practically possible 180 degrees from each other and mounted on a rotor (not shown) relative to a track of image capturing portion 314. Image capturing portion 314 can be operable to rotate 360 degrees during image acquisition. Image capturing portion 314 may rotate around a central point or axis, allowing image data of the patient to be acquired from multiple directions or in multiple planes. Surgical navigation system 306 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 306 can include C-arm fluoroscopic imaging systems, which can generate three-dimensional views of a patient. The position of image capturing portion 314 can be precisely known relative to any other portion of an imaging device of navigation system 306. In some embodiments, a precise knowledge of the position of image capturing portion 314 can be used in conjunction with a tracking system 316 to determine the position of image capturing portion 314 and the image data relative to the patient.

Tracking system 316 can include various portions that are associated or included with surgical navigation system 306. In some embodiments, tracking system 316 can also include a plurality of types of tracking systems, such as, for example, an optical tracking system that includes an optical localizer, such as, for example, sensor array 302 and/or an EM tracking system that can include an EM localizer. Various tracking devices can be tracked with tracking system 316 and the information can be used by surgical navigation system 306 to allow for a display of a position of an item, such as, for example, a patient tracking device, an imaging device tracking device 320, and an instrument tracking device, such as, for example, emitter array 304, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to a computer 318 where they may be forwarded to computer 308. Image transfer may be performed over a standard video connection or a digital link including wired and wireless. Computer 308 provides the ability to display, via monitor 310, as well as save, digitally manipulate, or print a hard copy of the received images. In some embodiments, images may also be displayed to the surgeon through a heads-up display.

In some embodiments, surgical navigation system 306 provides for real-time tracking of the position of bone fastener 100 relative to driver 12 and/or tissue can be tracked. Sensor array 302 is located in such a manner to provide a clear line of sight with emitter array 304, as described herein. In some embodiments, fiducial markers 322 of emitter array 304 communicate with sensor array 302 via infrared technology. Sensor array 302 is coupled to computer 308, which may be programmed with software modules that analyze signals transmitted by sensor array 302 to determine the position of each object in a detector space.

Driver 12 is configured for use with a guide member, such as, for example, an end effector 200 of robotic arm R. End effector 200 includes an inner surface 202 that defines a cavity, for example, a channel 204. Channel 204 is configured for passage of bone fastener 100 and disposal of driver 12. Robotic arm R includes position sensors (not shown), similar to those referenced herein, which measure, sample, capture and/or identify positional data points of end effector 200 in three dimensional space for a guide-wireless insertion of bone fasteners 100 with tissue. In some embodiments, the position sensors of robotic arm R are employed in connection with surgical navigation system 306 to measure, sample, capture and/or identify positional data points of end effector 200 in connection with surgical treatment, as described herein. The position sensors are mounted with robotic arm R and calibrated to measure positional data points of end effector 200 in three dimensional space, which are communicated to computer 308.

In assembly, operation and use, spinal implant system 10, similar to the systems and methods described herein, is employed with a surgical procedure, for example, a treatment of an applicable condition or injury of an affected section of a spinal column and adjacent areas within a body. In some embodiments, spinal implant system 10 is employed with a surgical procedure for treatment of an SI joint of a patient. In some embodiments, one or all of the components of spinal implant system 10 can be delivered or utilized as a pre-assembled device or can be assembled in situ. Spinal implant system 10 may be completely or partially revised, removed or replaced.

In use, to treat an SI joint of a patient, a medical practitioner obtains access to a surgical site in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby the SI joint is accessed through a mini-incision, or a sleeve that provides a protected passageway to the area. Once access to the surgical site is obtained, the particular surgical procedure can be performed for treating the spine disorder.

Figure 17:
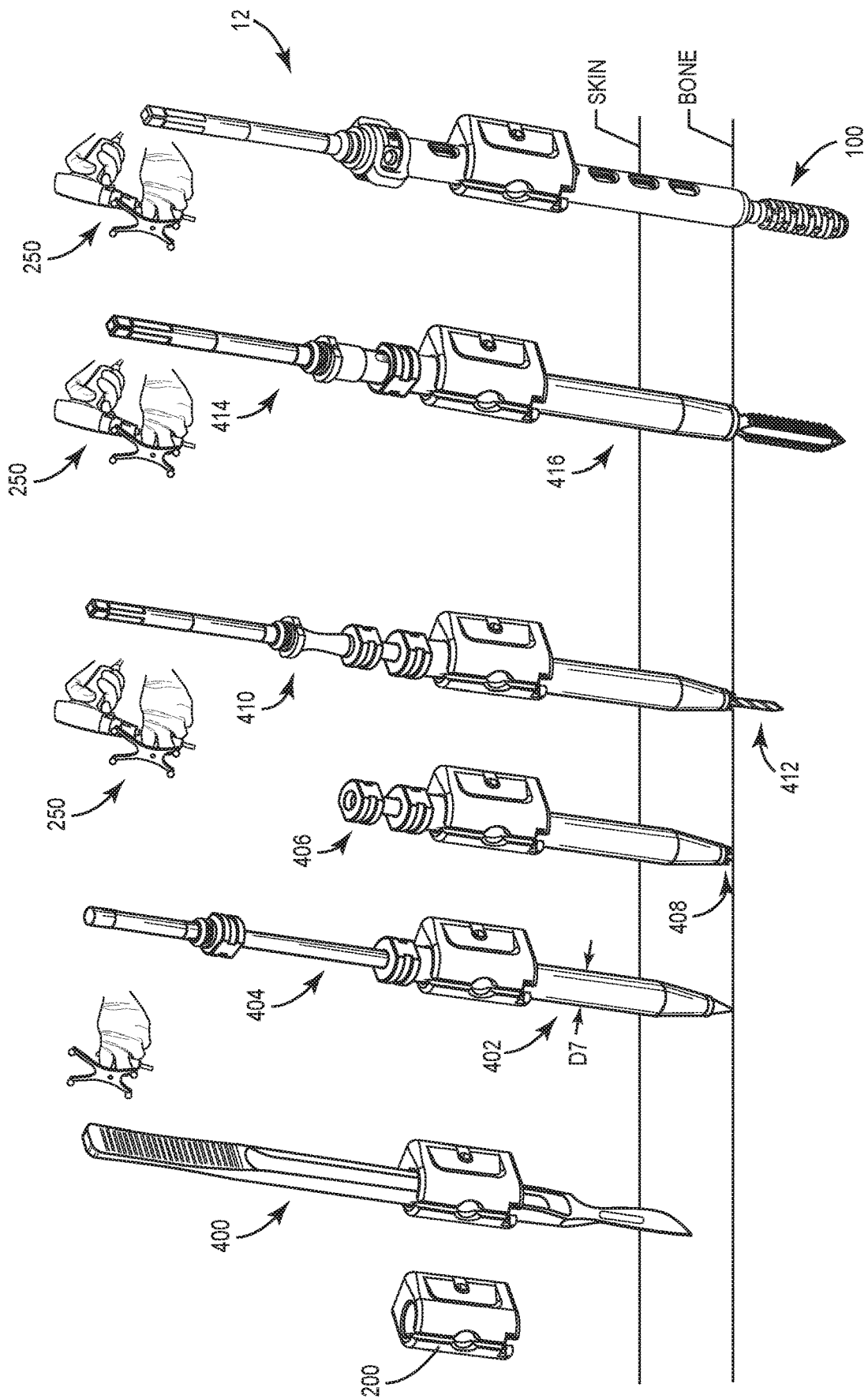
FIG. 17 is a perspective view of components of one embodiment of a surgical system in accordance with the principles of the present disclosure.
Figure 18:
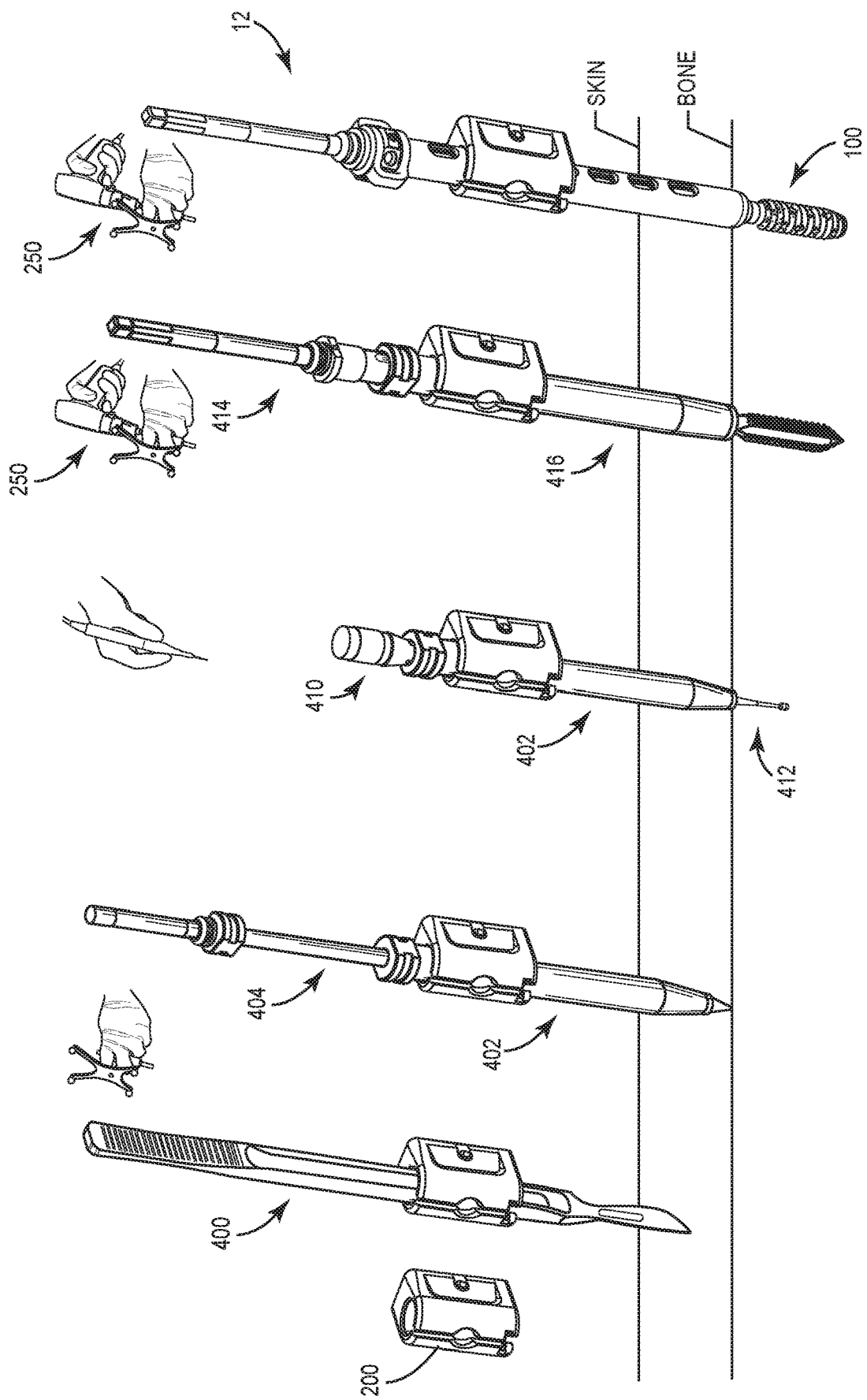
FIG. 18 is a perspective view of components of one embodiment of a surgical system in accordance with the principles of the present disclosure.

In some embodiments, a scalpel 400 is oriented for disposal with end effector 200 of robotic arm R, as described herein. An incision is made in the body of a patient with scalpel 400, as shown in FIGS. 17 and 18, which creates a surgical pathway for implantation of components of spinal implant system 10. A speculum (not shown) can be employed to assist in creating the surgical pathway. A preparation instrument (not shown) can be employed to prepare tissue surfaces as well as for aspiration and irrigation of a surgical region. A cannula 402 is inserted into end effector 200 and is inserted into the surgical pathway. A dilator 404 is inserted into cannula 402 to expand the surgical pathway. In some embodiments, a drill guide 406 and a drill guide anchor 408 can be inserted into cannula 402 to assist in the control and guidance of a drill 410, as shown in FIG. 17. Drill guide 406 can be securely docked by employing a slap hammer (not shown) and tapping on drill guide 406. Drill 410 is paired with a selected drill bit 412 and inserted into cannula 402.

Figures 15, 16:
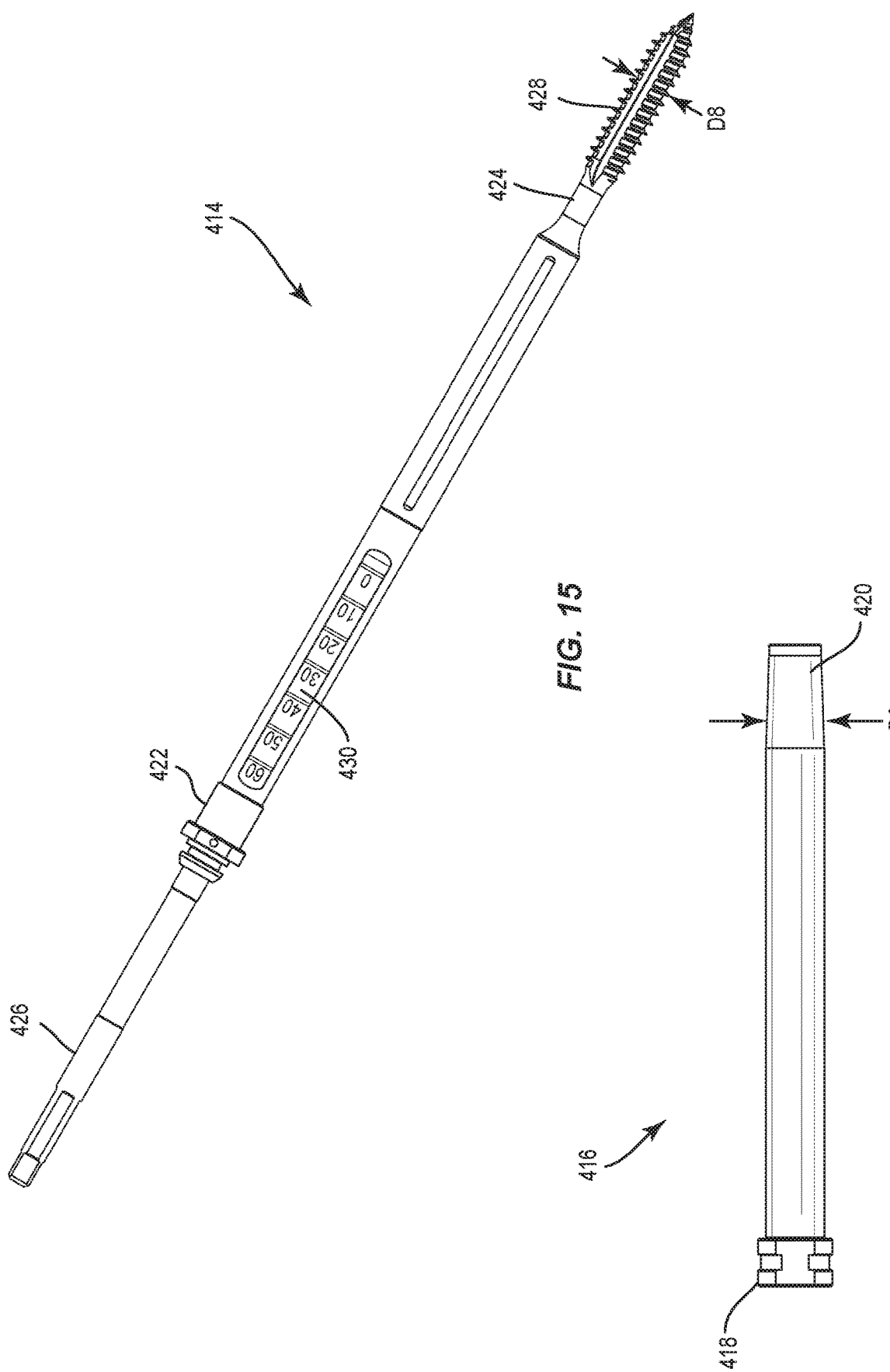
FIG. 15 is a perspective view of components of one embodiment of a surgical system in accordance with the principles of the present disclosure.
FIG. 16 is a side view of components of one embodiment of a surgical system in accordance with the principles of the present disclosure.

Pilot holes (not shown) are made with drill 410 in selected areas of bone, for example, in ilium (I), sacrum (S) and/or sacroiliac joint (J) for receiving bone fasteners 100. Drill 410, drill guide 406 and drill guide anchor 408 are removed from cannula 402 and a tap 414 is inserted into a cannula 416. Cannula 416 is configured as a tissue protector for tap 414. As shown in FIGS. 16 and 17, cannula 416 includes a proximal end 418 and a distal end 420. An internal diameter D6 at end 420 is greater than an internal diameter D7 of cannula 402. Internal diameter D6 is greater than internal diameter D7 to accommodate a tip 428 of tap 414.

Tap 414 includes a proximal end 422 and a distal end 424. End 422 includes a portion 426 configured to facilitate connection of tap 414 with actuator/drill 250, as shown in FIG. 14. In some embodiments, tap 414 includes quick connect surfaces or keyed geometry, such as, for example, triangle, hex, square or hexalobe to facilitate connection with actuator 250. End 424 includes a threaded tip, such as an awl tip 428. Tip 428 has an outer diameter D8. End 422 includes indicia 430 configured to visually indicate the depth of tap 414 when contacting bone. In some embodiments, the indicia can include a notch, slot, bead, detent, bump, print, label, score, color coding and/or increments of depth in millimeters, centimeters or inches disposed on tap 414. Tap 414 is aligned with pilot holes and tapped to a selected depth to correlate with a length of bone fastener 100. Tap 414 and cannula 416 are removed.

Drive 80 is aligned with end 108 of bone fastener 100 and screw 64 of inner sleeve 50 is aligned with inner threaded surface 102, as shown in FIG. 2. Driver 12 is axially translated to connect to bone fastener 100 in a non-locking configuration, as shown in FIG. 6. Drive 80 is engaged with socket 104 and wheel 32 is manipulated for rotation such that inner sleeve 50 rotates screw 64 relative to and independent of outer sleeve 14. Rotation of screw 64 creates a threaded engagement between outer threaded surface 66 of screw 64 and inner threaded surface 102 of bone fastener 100 to retain and/or draw bone fastener 100 into engagement with driver 12 in a locking configuration, as shown in FIG. 5.

Driver 12 is oriented for disposal with end effector 200 of robotic arm R, as described herein. The assembly of driver 12/bone fastener 100 is disposed with channel 204 for implantation of one or more bone fasteners 100 with sacroiliac joint J employing robotic arm R and/or surgical navigation system 306, as described herein. Actuator 250 is connected with inner shaft 72 and drive 80 engages bone fastener 100, as described herein, and inner shaft 72 and outer sleeve 14 are rotated to drive, torque, insert or otherwise connect bone fastener 100 with adjacent tissue. Screw 64 remains releasably fixed with inner threaded surface 102, independent of inner shaft 72 and outer sleeve 14 rotation and/or engagement or friction with end effector 200 to resist and/or prevent disengagement or unthreading of screw 64 from inner threaded surface 102. In some embodiments, driver 12 is manipulated to deliver one or more bone fasteners 100 to a surgical site including sacroiliac joint J.

Sensor array 302 receives signals from navigation component 300 to provide a three-dimensional spatial position and/or a trajectory of the assembly of driver 12/bone fastener 100, which may be disposed with end effector 200, relative to sacroiliac joint J and/or components of spinal implant system 10 for display on monitor 310. Wheel 32 is manipulated for rotation such that inner sleeve 50 and screw 64 rotate relative to outer sleeve 14, and outer threaded surface 66 disengages with inner threaded surface 102. Driver 12 is translated away from implant 100 to unthread driver 12 from inner threaded surface 102, and driver 12 is considered in the non-locking configuration relative to bone fastener 100, as shown in FIG. 2.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone fasteners for use with a single vertebral level or a plurality of vertebral levels.

In some embodiments, one or more bone fasteners, as described herein, may be engaged with tissue in various orientations, such as, for example, series, parallel, offset, staggered and/or alternate vertebral levels. In some embodiments, the bone fasteners may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
    an outer sleeve defining a longitudinal axis and including an inner surface that defines a cavity;
    an inner shaft fixed with the outer sleeve such that the inner shaft is prevented from translating relative to the outer sleeve in opposite directions along the longitudinal axis, the inner shaft extending within the cavity, the inner shaft including a drive engageable with a first mating surface of a bone fastener; and
    an inner sleeve disposed between the inner shaft and the outer sleeve, the inner sleeve being axially fixed and rotatable relative to the outer sleeve, the inner sleeve including an element connectable with a second mating surface of the bone fastener, the inner sleeve comprising a proximal end including an actuator and a distal end including the element, the actuator being rotatable relative to the outer sleeve and prevented from translating relative to the outer sleeve in opposite directions along the longitudinal axis.

2. A surgical instrument as recited in claim 1, wherein the element includes a threaded outer surface.

3. A surgical instrument as recited in claim 1, wherein the element includes a threaded outer surface being disposed adjacent a distal most position of the inner sleeve.

4. A surgical instrument as recited in claim 1, wherein the drive defines a hexalobular cross section of the inner shaft.

5. A surgical instrument as recited in claim 1, wherein the first mating surface includes a hexalobular socket and the drive comprises a hexalobular portion engageable with the socket.

6. A surgical instrument as recited in claim 1, wherein the second mating surface includes an inner threaded surface of the bone fastener and the element comprises a threaded outer surface engageable with the inner threaded surface.

7. A surgical instrument as recited in claim 1, wherein the element and the drive are disposed in a serial orientation.

8. A surgical instrument as recited in claim 1, wherein the outer sleeve includes bifurcated arms defining a collar, the actuator being disposed within the collar.

9. A surgical instrument as recited in claim 8, wherein the actuator includes a wheel that is fixed directly to the inner sleeve such that the inner shaft is spaced apart from the wheel.

10. A surgical instrument as recited in claim 1, wherein the actuator is integrally connected with the inner sleeve.

11. A surgical instrument as recited in claim 1, wherein the distal end includes a tapered tip that extends to the element.

12. A surgical instrument as recited in claim 1, wherein the inner sleeve includes a tip that extends to the element, the tip including a tapered portion having a decreasing diameter and an axial portion having a uniform diameter.

13. A surgical instrument as recited in claim 12, wherein the axial portion has a diameter equal to a minor diameter of the bone fastener.

14. A surgical instrument comprising:
    an outer sleeve defining a longitudinal axis and including an inner surface that defines an axial cavity;

an inner shaft fixed with the outer sleeve such that the inner shaft is prevented from translating relative to the outer sleeve in opposite directions along the longitudinal axis, the inner shaft extending within the cavity, the inner shaft including a hexalobular drive tip engageable with a hexalobular socket of a bone fastener; and an inner sleeve disposed between the inner shaft and the outer sleeve in a relative coaxial orientation, the inner sleeve being axially fixed and rotatable relative to the outer sleeve, the inner sleeve including a proximal end having a rotatable actuator and a threaded tip connectable with an inner threaded surface of the bone fastener, the actuator being permanently prevented from translating relative to the outer sleeve in opposite directions along the longitudinal axis.

15. A spinal implant system comprising:

a surgical instrument including an outer sleeve, an inner shaft fixed with the outer sleeve, and an inner sleeve, the outer sleeve defining a longitudinal axis, the inner shaft including a drive, the inner shaft being prevented from translating relative to the outer sleeve in opposite directions along the longitudinal axis, the inner sleeve being rotatable relative to the outer sleeve and including an element, the inner sleeve comprising a proximal end including an actuator and a distal end including the element, the actuator being rotatable relative to the outer sleeve and prevented from translating relative to the outer sleeve in opposite directions along the longitudinal axis;

a sacro-iliac bone screw having an inner surface and an outer threaded surface, the inner surface including a socket engageable with the drive in a torque interface and an inner threaded surface connectable with the element in a connection interface; and a guide member including an inner surface that defines a cavity configured for disposal of the outer sleeve and an image guide being oriented relative to a sensor to communicate a signal representative of a position of the guide member.

16. A spinal implant system as recited in claim 15, wherein the guide member including an end effector of a robotic arm.

17. A spinal implant system as recited in claim 15, further comprising a tracking device including the sensor that receives the signal and communicates with a processor to generate data for display of an image from a monitor, the image representing position of the guide member relative to tissue.

18. A spinal implant system as recited in claim 15, wherein an entire length of the outer threaded surface is threaded.

19. A spinal implant system as recited in claim 15, wherein the bone screw defines a longitudinal cavity and a plurality of lateral openings in communication therewith.

20. A spinal implant system as recited in claim 15, wherein the inner sleeve includes a tapered tip.

* * * * *